US00PP32701P3

(12) United States Plant Patent
Patel et al.

(10) Patent No.: US PP32,701 P3
(45) Date of Patent: Dec. 29, 2020

(54) BLUEBERRY PLANT NAMED 'ZZ04115'

(50) Latin Name: ***Vaccinium corymbosum* hybrid**
Varietal Denomination: ZZ04115

(71) Applicant: The New Zealand Institute for Plant and Food Research Limited, Auckland (NZ)

(72) Inventors: Narandra Patel, Hamilton (NZ); Jessica Scalzo, Corindi (AU)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 16/602,121

(22) Filed: Aug. 8, 2019

(65) Prior Publication Data

US 2020/0068761 P1 Feb. 27, 2020

Related U.S. Application Data

(60) Provisional application No. 62/723,225, filed on Aug. 27, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08; A01H 6/36
See application file for complete search history.

*Primary Examiner* — Annette H Para
(74) *Attorney, Agent, or Firm* — Leydig, Voit & Mayer, Ltd.

(57) ABSTRACT

A new and distinct southern high bush blueberry variety is described. The variety results from selection among a population of seedlings derived from the controlled crossing of the blueberry varieties B7-8-1 (seed parent) (not patented) and D110 (pollen parent) (not patented). The fruit of this new variety has an attractive appearance characterised by outstanding fruit quality with a good bloom, very large size, light blue skin colour and mid-season harvests. The new variety appears suitable for the fresh fruit market.

4 Drawing Sheets

Genus and species plant claimed: *Vaccinium corymbosum* hybrid.

Variety denomination: 'ZZ04115'.

BACKGROUND OF THE INVENTION

The variety resulted from selection among a population of seedlings derived from a controlled cross carried out in 2004 between B7-8-1 (seed parent) (not patented) and D110 (pollen parent) (not patented) located at Ruakura, Hamilton, New Zealand. 'ZZ04115' was identified in 2006 as having potential as a new variety due to its attractive, very large, light blue fruit with good flavour. It was asexually propagated by cuttings in 2007 and the resulting plants were subsequently found to be true to type demonstrating that the characteristics of the new variety are stable and transmitted without change through succeeding generations. Since the initial propagation in vitro propagation has also been carried out successfully.

SUMMARY OF THE INVENTION

'ZZ04115' is characterised by its attractive, very large, light blue fruit with good flavour which harvests around mid-season. 'ZZ04115' is distinguished from a number of other varieties and by its parents by the following characteristics:

The fruit of 'ZZ04115' are larger than those of its patents, 'B7-8-1' (not patented) and firmer than 'D110' (not patented).

The bush shape of 'ZZ04115' is spreading while the 'O'Neal' is semi-upright. 'Misty' begins flowering earlier than 'ZZ04115'.

BRIEF DESCRIPTION OF THE DRAWINGS

The accompanying photographs show typical specimens of the plant, flower and fruit of the new variety as depicted in colours as nearly true as is reasonably possible to make the same in a colour illustration of this character. Unless otherwise specified, the photographs depict mature (6 year old) plant grown at, Motueka, New Zealand.

DETAILED DESCRIPTION

Figure 1:
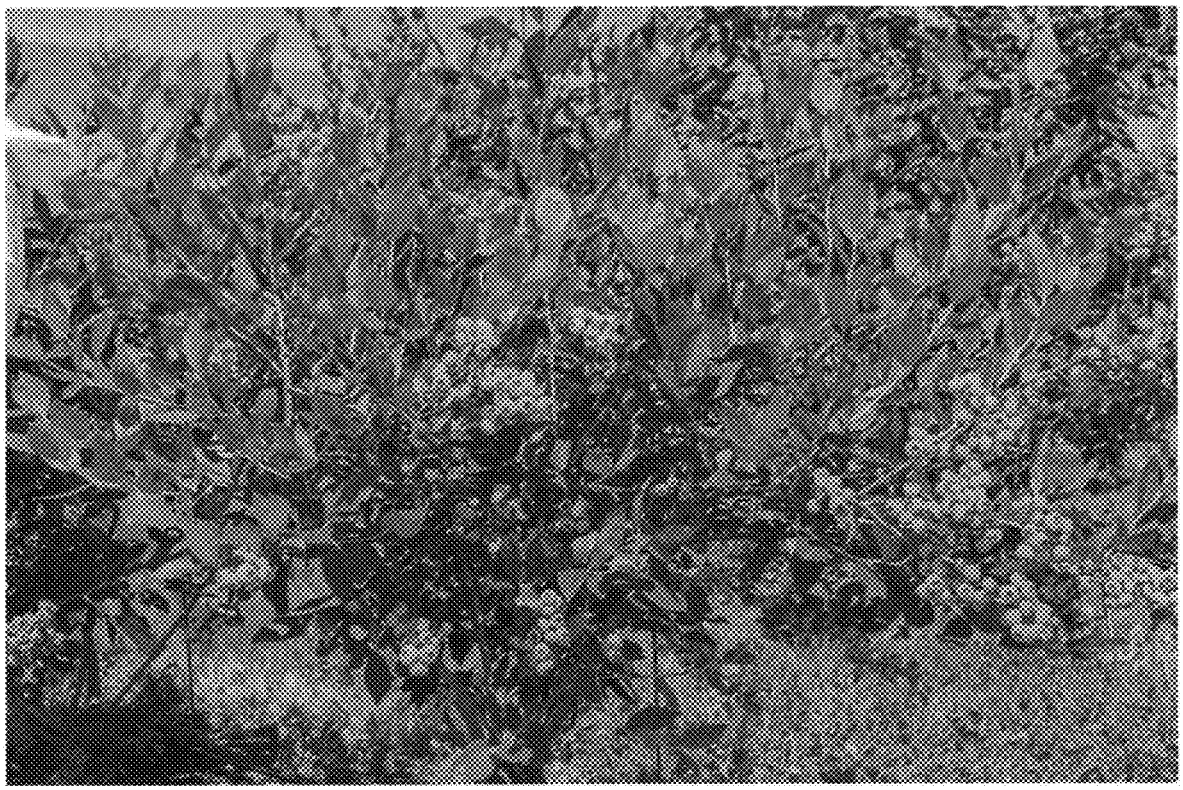
FIG. 1 shows a 6 year old bush of 'ZZ04115'.
Figure 2:
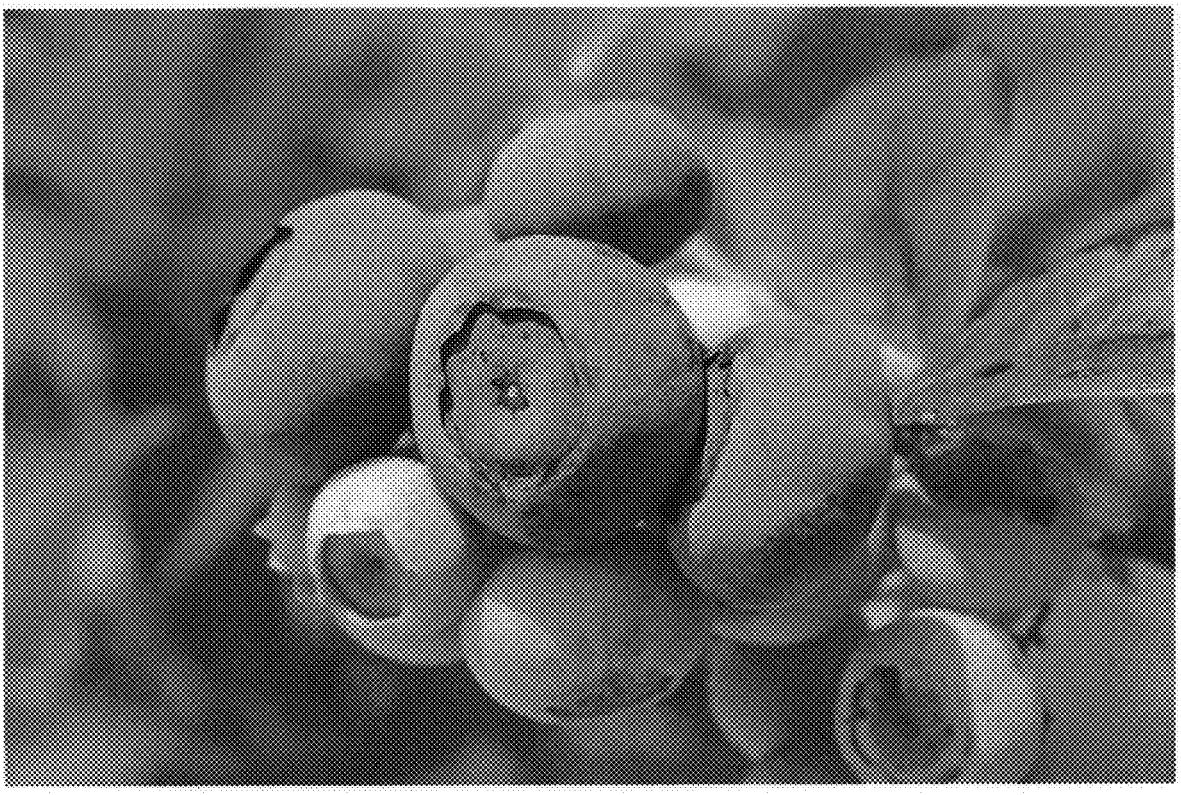
FIG. 2 shows fruit of 'ZZ04115' on 6 year old plant.
Figure 3:
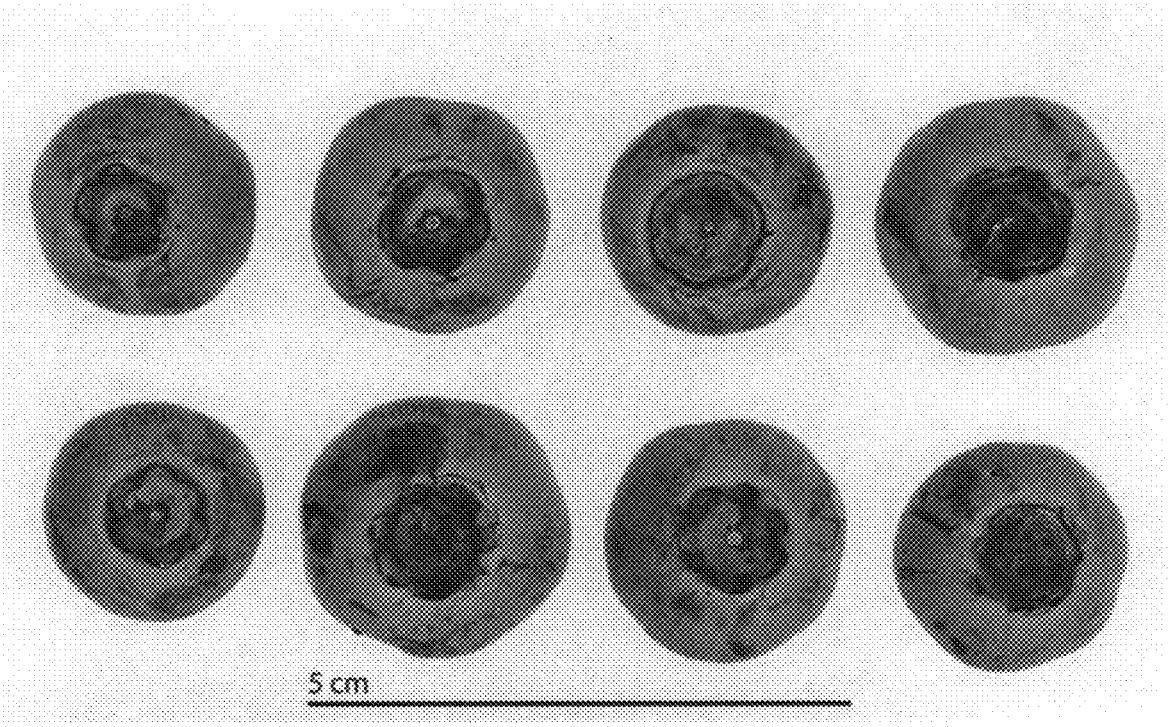
FIG. 3 shows fruit of 'ZZ04115' removed from the plant.
Figure 4:
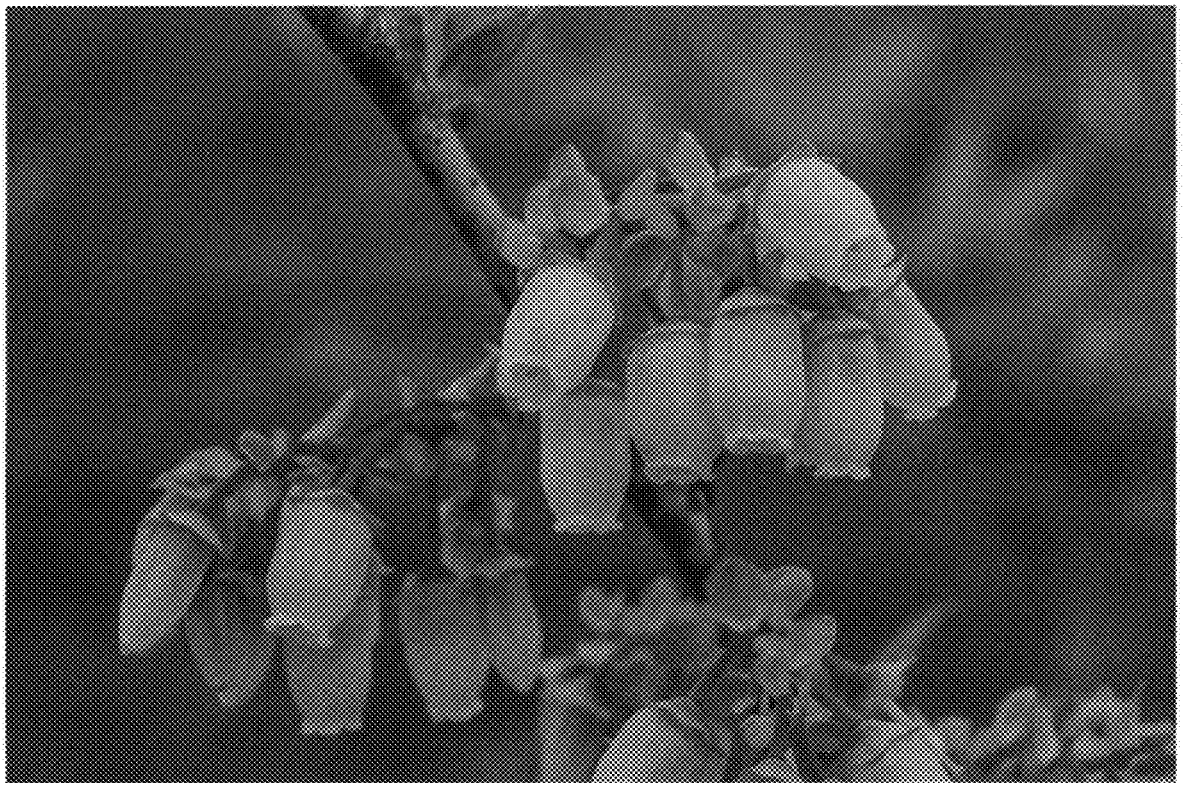
FIG. 4 shows flowers of 'ZZ04115'.

The observations, unless otherwise specified, were made in the 2015-2016, 2016-17 seasons on 5-6 year old plants grown at, Motueka, New Zealand. All dimensions in millimetres, weights in grams (unless otherwise stated). Colour terminology is in accordance with The Royal Horticultural Society Colour Charts (R.H.S.C.C.) fifth edition.

Plant and foliage: This plant is generally spreading in growth habit. The surface texture of one year old canes are moderately rough while the surface texture of mature canes (of three year old wood) is rough and peeling; the colour of immature canes is near yellow-green 152D. The colour of the bark of mature canes is near greyed-green 197C. The mature leaf is lanceolate in shape and typically averages 58 mm in length and approximately 27 mm in width. The margins are generally entire, with slight glossiness on the upper surface. Pubescence is absent from the leaf upper and lower surface. The upper surface of the leaf is near yellow-green 147A and the lower surface near green 138A in colour. The petiole typically averages 3.5 mm in length.

Inflorescence: The average number of flower/cluster are approximately 10 with an observed range of 5-16 flowers. Flowers are generally clustered and the typical flower has an average flower length of 12.7 mm and the diameter of the corolla aperture averages 4.3 mm. The average diameter of the corolla tube is 7 mm. The style length is approximately 9 mm. The main colour of the petals on fully open mature flowers is near white N155C. The pedicel length averages 8.6 mm, with peduncle average length 11 mm.

Fruit: The fruit are of very large size, averaging approximately 3.4 g (observed range 2.0-4.5 g) and clustered with an average of 10 berries/cluster. Fruiting occurs on one year old shoots only; flowers do not occur on current season's shoots. The time of beginning of fruit ripening on one year old shoots is mid-season, similar to that on 'Nui'. Generally fruit is flat in shape with an average diameter of approximately 19 mm (observed range 16-22 mm). Ripe fruit generally has a skin colour of near violet-blue 98A with bloom intact and near blue 103A with bloom removed. The bloom is moderately strong. Internal flesh colour of ripe fruit is near greyed-green 194D. The calyx aperture is round in shape on a ripe berry and has an average diameter of 8 mm. The depth of the calyx basin is very shallow. The attitude of the incurving sepals tends to be horizontal. The pedicel scar is small and generally dry. The fruit is firm and flavour moderately acidic, the fruit sweetness (Brix level) averaged 11.04. Yield is high, averaging approximately 7 Kg per plant. The self-compatibility of the new variety has not been tested by self-crossing the variety. However, it is recommended to associate the plant with other varieties with similar flowering timing to maximise pollination and fruit set.

Events: Vegetative bud burst occurred around 15 September under New Zealand growing conditions. Time of beginning flowering mid-September, similar to or a few days before 'Nui'.

*Maturity period.*—Mid-season; fruit commenced ripening on trial plants at Motueka, New Zealand, early December, slightly later than 'Nui' with 50% of the crop ripe around 17 December.

Pest and disease: The plant does not seem to be susceptible to rust (*Pucciniastrum vaccinii*). No symptoms of anthracnose or *Botryosphaeria* have been observed under New Zealand growing conditions.

Additional description: The variety has been observed to be suited to production of blueberries for fresh consumption. The plant cold hardiness according to the American zone classification has not been determined. However, the chilling requirement of 'ZZ04115' has been estimated to be between 1000+ hours.

The invention claimed is:

1. A new and distinct blueberry plant substantially as illustrated and described.

* * * * *